ically hindered carbinol. For example, Tedeschi et al. disclose in U.S. Pat. No. 3,709,946 the preparation of ethynyl-β-ionol by reacting β-ionone with acetylene in a liquid ammonia-aliphatic ether solvent system at elevated temperatures and pressures.

United States Patent [19]

Wiederkehr

[11] 4,147,886

[45] Apr. 3, 1979

[54] PROCESS FOR THE PREPARATION OF ETHYNYL-β-IONOL

[75] Inventor: Hermann Wiederkehr, Flüh, Switzerland

[73] Assignee: Hoffmann-La Roche Inc., Nutley, N.J.

[21] Appl. No.: 808,509

[22] Filed: Jun. 21, 1977

[30] Foreign Application Priority Data

Jul. 15, 1976 [CH] Switzerland ................. 9084/76

[51] Int. Cl.² ............................................. C07C 29/00
[52] U.S. Cl. .................................................... 568/824
[58] Field of Search ..................... 260/617 E; 568/824

[56] References Cited

U.S. PATENT DOCUMENTS

| | | | |
|---|---|---|---|
| 2,672,481 | 3/1954 | Weisler et al. | 260/617 E |
| 2,779,799 | 1/1957 | Hamlin | 260/617 E |
| 2,789,130 | 4/1957 | Kimel | 260/617 E |
| 2,806,067 | 9/1957 | Monroe et al. | 260/617 E |
| 2,919,281 | 12/1959 | Chodroff et al. | 260/617 E |
| 3,019,265 | 1/1962 | Eschinazi | 260/617 E |
| 3,496,240 | 2/1970 | Sturyenegger | 260/617 E |
| 3,709,946 | 1/1973 | Tedeschi et al. | 260/617 E |
| 3,801,653 | 4/1974 | Pasedach et al. | 260/617 E |

FOREIGN PATENT DOCUMENTS

| | | |
|---|---|---|
| 1173457 | 7/1964 | Fed. Rep. of Germany. |
| 1232573 | 1/1967 | Fed. Rep. of Germany. |
| 1768877 | 8/1971 | Fed. Rep. of Germany. |
| 2329145 | 12/1974 | Fed. Rep. of Germany. |
| 852945 | 11/1960 | United Kingdom. |
| 1161150 | 8/1969 | United Kingdom. |

OTHER PUBLICATIONS

Oroshnik et al., "J.A.C.S.", vol. 71, pp. 2062–2065 (1949).
Houben-Weyl, "Methoden der Organ. Chemie", Bd. VII/2b, Teil II, pp. 1974–1975 (1976).
A. G. Viehe "Chem. of Acetylenes", pp. 225–226 (1969), Marcel Dekker, New York, N.Y.
Tedeschi et al., "J. Org. Chem", vol. 28, pp. 1740–1743 (1963).
Shachat et al., "J. Org. Chem.", vol. 27, pp. 1498–1504 (1962).

*Primary Examiner*—Norman Morgenstern
*Attorney, Agent, or Firm*—Jon S. Saxe; Bernard S. Leon; William H. Epstein

[57] ABSTRACT

A process for the preparation of ethynyl-β-ionol involving the reaction of acetylene and β-ionone in the presence of an alkali metal hydroxide in liquid ammonia is disclosed.

2 Claims, No Drawings

PROCESS FOR THE PREPARATION OF ETHYNYL-β-IONOL

BACKGROUND

The present invention is concerned with a process for the manufacture of ethynyl-β-ionol. Ethynyl-β-ionol is an intermediate used in the preparation of vitamin A.

It has surprisingly been found that ethynyl-β-ionol is obtained in yields of nearly 100%, when β-ionone is reacted with acetylene in the presence of an alkali metal hydroxide in liquid ammonia at a temperature between about −40° and about +30° C.

Conventional alkali metal hydroxides may be employed in the process of this invention with sodium and potassium hydroxide being preferred. Potassium hydroxide is particularly preferred.

A preferred embodiment of the process in accordance with the invention consists in that the reaction is carried out in the temperature range between about −20° and about +5° C., preferably at about 0° C., and at pressures varying from 1.5 atmospheres to 9.5 atmospheres, preferably 8 atmospheres.

The alkali metal hydroxide is generally employed in catalytic amounts varying from about 0.1 mol.% to about 20 mol.%, preferably in an amount of 10 mol.% based on the β-ionone quantity. The alkali metal hydroxide may be employed in larger amounts, i.e., up to 100 mol%, although no significant advantages are gained thereby.

The alkali metal hydroxide is generally used as an aqueous or lower alkanol solution. The term lower alkanol as used herein connotes straight and branched chain alcohols having from 1–6 carbon atoms. The preferred lower alkanoic solution employed herein is a methanolic solution. The concentration of these solutions can vary from about 5 and about 60 wt.%, preferably between about 20 and 50 wt.%, most preferably about 45 wt.%. The alkali metal hydroxide may also be used in solid form, or as a suspension in a suitable liquid.

The process of this invention may be carried out either batchwise or continuously, with the continuous mode being preferred.

After carrying out the reaction, the remaining amount of catalyst is neutralized, for example with a mineral acid or a lower alkanoic acid. Preferred acids that may be employed are sulfuric, nitric, hydrochloric, acetic and the like.

EXAMPLE 1

680 g of ammonia are charged to a reaction vessel pre-cooled to −40° C. Thereupon 2 ml of a 45% aqueous solution of potassium hydroxide are added with stirring. Acetylene is conducted into the solution, which is maintained at −40° C., at a velocity of 4 liters per minute. The excess acetylene is allowed to escape through an outlet. After 15 minutes, 10 g of β-ionone are allowed to flow into the reaction vessel with intensive stirring. Thereupon, additional acetylene is conducted into the reaction solution over a period of 5 hours with at a velocity of 4 liters per minute. 100 ml of diethyl ether are then added at −40° C. with the ammonia being cautiously evaporated off and the reaction solution is subsequently warmed to about 10° C. The aqueous potassium hydroxide solution is separated off and 100 ml of water are added to the organic phase. 50% acetic acid is then allowed to drop in while stirring until the pH-value reaches 7. The phases are then separated, the aqueous phase washed once with 200 ml of diethyl ether and the ether phases combined. The diethyl ether solution is dried over sodium sulfate and subsequently concentrated on a rotary evaporator at 40° C., and under reduced pressure. The yield of ethynyl-β-ionol is 99%, based on the reacted amount of β-ionone. The conversion amounts to 95%.

EXAMPLE 2

680 g of ammonia are charged into a pre-cooled reaction vessel. After achieving an internal temperature of 0° C., about 290 g of acetylene are forced into the reactor, which corresponds to an end pressure of about 7.2 atm at 0° C. During the entire reaction acetylene is forced into the reactor with 7.2 atm. of pressure. The stirring velocity is regulated at 750 revolutions/minute. 5 ml of 45% potassium hydroxide solution and 100 g of β-ionone are subsequently dosed into the reactor. After 30 and 60 minutes, 5 ml of 45% potassium hydroxide solution in each case are again dosed in. The reaction is completed after 3 hours. 200 ml of toluene are dosed into the reaction vessel and subsequently the ammonia and the excess acetylene are relieved through an absorption tower. As soon as the reactor is completely relieved of pressure and the temperature has reached 0° C., the reactor is emptied and rinsed with 200 ml of toluene. The toluene solution is warmed to about 10° C. The aqueous potassium hydroxide phase is separated off and 500 ml of water are added to the organic phase for the neutralization. The organic phase slowly neutralized to pH 7 with 50% acetic acid while stirring at 10° C. The phases are separated and the aqueous phase is washed once with 300 ml of toluene. The combined organic phases are dried with sodium sulfate and subsequently concentrated on the rotary evaporator at 40° C. and maximum 0.5 mm. There is obtained ethynyl-β-ionol in a yield of 98%, based on the reacted β-ionone (conversion 95%).

I claim:

1. A process for the preparation of ethynyl-β-ionol which comprises reacting β-ionone with acetylene in the presence of an alkali metal hydroxide in liquid ammonia at a temperature between about −40° and about +30° C.

2. The process of claim 1 wherein said alkali metal hydroxide is selected from the group consisting of potassium hydroxide and sodium hydroxide.